(12) United States Patent
Tazawa et al.

(10) Patent No.: US 6,616,928 B1
(45) Date of Patent: *Sep. 9, 2003

(54) ACTIVE OXYGEN SCAVENGER AND CANCER CHEMOPREVENTER FROM GRIFOLA

(75) Inventors: Kenji Tazawa, Toyama (JP); Yasuo Odaira, Niigata (JP); Masataka Watanabe, Tochigi (JP)

(73) Assignee: Yukiguni Maitake Co., Ltd., Niigata (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/421,572

(22) Filed: Oct. 20, 1999

(30) Foreign Application Priority Data

Oct. 20, 1998 (JP) .......................................... 10-297781
Sep. 28, 1999 (JP) .......................................... 11-275197

(51) Int. Cl.[7] .............................................. A61K 35/78
(52) U.S. Cl. .................................. 424/195.15; 424/725
(58) Field of Search .......................... 424/195.15, 278.1, 424/94.1, 195.1, 725; 530/371; 435/223, 171

(56) References Cited

U.S. PATENT DOCUMENTS

| | | | | |
|---|---|---|---|---|
| 5,595,756 A | * | 1/1997 | Bally et al. ................. | 424/450 |
| 5,854,404 A | | 12/1998 | Nanba et al. ............... | 532/424 |

FOREIGN PATENT DOCUMENTS

| | | | | |
|---|---|---|---|---|
| JP | 59210901 | | 11/1984 | |
| JP | 62209091 | | 9/1987 | |
| JP | 03117467 | * | 5/1991 | ............. A23L/1/28 |
| JP | 5317016 | | 12/1993 | |
| JP | 05317016 | * | 12/1993 | ............. A23K/1/16 |
| JP | 06065575 | | 3/1994 | |
| JP | 09238697 | | 9/1997 | |
| JP | 1042822 | | 2/1998 | |
| JP | 10042822 | * | 2/1998 | ............. A23L/1/212 |

OTHER PUBLICATIONS

Garuda International Web Site: http://www.cowcium.com/dmaiext.htm, Oct. 1998.*
Gura, T. Systems for Identifying New Drugs are Often Faulty; Science, vol. 278, 1997 pp. 1041–1042.*
Kelloff, G. J., Boone, C. W., Malone, W. F., Steele, V. E., Recent results in preclinical and clinical drug development of chemopreventive agents at the National Cancer Institute, in *Cancer Chemoprevention*, pp. 41–55, CRC Press (1992).
Nanba, H., Maitake Mushroom immune therapy to prevent from cancer growth and metastasis, *Explore!* Vol 6 No. 1, pp. 16–18, 1995.
Benner, S. E., Pastorino, U., Lippman, S. M., Hong, W. K., Second international cancer chemoprevention conference, *Cancer Research* Vol 54, pp. 854–856, 1994.
McNamee, D., New society focuses on cancer chemoprevention, *The Lancet*, Vol 346, p. 1222, 1995.

* cited by examiner

*Primary Examiner*—Brenda Brumback
*Assistant Examiner*—Patricia A Patten
(74) *Attorney, Agent, or Firm*—Davidson, Davidson & Kappel, LLC

(57) ABSTRACT

The present invention relates to an active oxygen scavenging agent and a cancer chemopreventing agent both comprising a dried Grifola, a dry Grifola powder and/or a Grifola extract, and to a food or animal feed comprising the active oxygen scavenging agent or the cancer chemopreventing agent.

4 Claims, 4 Drawing Sheets

ACTIVE OXYGEN SCAVENGER AND CANCER CHEMOPREVENTER FROM GRIFOLA

BACKGROUND OF THE INVENTION

1. Field of the Invention

The present invention relates to an active oxygen scavenging agent and a cancer chemopreventing agent both which can prevent biological damage in living bodies caused by excess active oxygen and can also prevent the development of cancer, and also relates to a food or animal feed comprising the active oxygen scavenging agent and/or the cancer chemopreventing agent.

2. Description of the Prior Art

Oxygen is essential for most of the animals and plants on the earth to live. However, excess oxygen exerts a harmful action called "oxygen toxicity", which is likely to damage a living body, and therefore upon recently has been focused on as a causative substance of the acceleration of aging and various diseases or disorders specific to adult people, including cancer.

Oxygen found in the atmosphere normally takes the form of a stable, so-called "triplet oxygen". Upon taking up into a living body, the oxygen is partially converted into a highly reactive substance called "active oxygen". Active oxygen is necessary for killing pathogenic viruses or bacteria invading into a living body, and plays an extremely important role in biophylaxis. However, it has become evident that excess active oxygen in a living body adversely acts on proteins, lipids and even nucleic acids to cause various kinds of damage in the living body, and therefore is a cause of the acceleration of aging and the development of various diseases, such as arteriosclerosis, diabetes, Alzheimer's disease and Crohn's disease.

The active oxygen species produced in a living body include: in a narrow sense, superoxide anion radical ($O_2^-$), hydrogen peroxide ($H_2O_2$), hydroxyl radical (.OH) and singlet oxygen ($^1O_2$); and in an broad sense, in addition to the above four species, alkoxy radical (LO.), lipid peroxy radical (LOO.), nitric oxide (NO) and peroxy nitrite ($ONOO^-$) which is a reaction product of nitrogen oxide and a superoxide.

As the scavengers for these active oxygen species, the following substances are known:

(1) superoxide dismutase (SOD)—for superoxide anion radicals;

(2) catalase, glutathione peroxidase, ascorbate peroxidase, and the like—for hydrogen peroxide;

(3) carotenoids, tocopherol and the like—for singlet oxide; and (4) tocopherol, flavonoids, ascorbic acid, glutathione, carotenoids and the like—for alkoxy radicals and lipid peroxy radicals.

These scavengers, however, have disadvantages. For example, superoxide dismutase (SOD) is difficult to be applied to experiments that use cells, animals and plants, because it is a protein. Other enzymatic scavengers, such as catalase for hydrogen peroxide, are also difficult to handle for the same reason as mentioned for SOD. Carotenoids, tocopherol and the like for singlet oxide have poor selective activity.

With respect to hydroxyl radicals (.OH), no specific scavenger is found, because hydroxyl radicals can react with various biocomponents in a diffusion-dependent mode. Mannitol, dimethyl sulfoxide (DMSO), ethanol, thiourea and the like are known to be scavengers for hydroxyl radicals. However, these substances are insufficient for scavenging hydroxyl radicals when used singly, and therefore the use of these substances in combination must be considered. Thus, up to now, no satisfactory scavenger has been developed.

On the other hand, a number of new methods for the diagnosis and treatment of cancer have been developed. Nevertheless, the number of deaths caused by cancer tends to increase on a worldwide basis. Therefore, in parallel to the extensive studies on cancer eradication, value is increasingly being placed upon studies on the prevention of cancer. The methodologies for the prevention of cancer are as follows:

(i) Identification and removal of carcinogenic substances; and (ii) Screening and active intake of cancer preventing substances.

Since there are innumerable chemical substances in the surroundings, it will take enormous labor and cost to identify and screen carcinogenic substances. Even if identified, it is probably impossible to eliminate the carcinogenic substances from the environment. Therefore, although it is still necessary to avoid the substances which are clearly shown to be involved in cancer development, it has been considered that the active intake of cancer preventing substances is very effective for cancer prevention.

Actually, the researchers of the National Cancer Institute of U.S.A. established a category "cancer chemoprevention", which is defined as an approach to inhibit the development and growth of cancer through administration of a certain substance. This approach has recently been studied intensively in most countries of the world including the U.S.A. However, as yet, no effective approach for the prevention of cancer has been found, and such an approach is demanded.

SUMMARY OF THE INVENTION

Under these circumstances, the present inventors have extensively screened the daily foods that have the scavenging activity against active oxygen species, particularly hydroxyl radicals. As a result, the inventors have found that Maitake and related mushrooms and derivatives thereof have an effective hydroxyl radical scavenging activity, as well as a superoxide anion radical scavenging activity and a superoxide dismutase (SOD)-like activity. This finding leads the accomplishment of the invention.

In addition to the active oxygen scavenging activity, the inventors have also examined daily foods on the cancer chemopreventing activity.

The research on the cancer chemopreventing activity takes more labor and cost compared to a tumor-growth inhibition test that is usually performed for the development of a anticancer agent or the like. This is because such a research requires a far longer period of time for the administration of test substances into test animals and for the observation of the pathologic process, and had to be performed under tightly controlled conditions for the test animals. Nevertheless, through such a research, the inventors have found that Maitake and related mushrooms and derivatives thereof have a cancer chemopreventing activity. This finding leads the accomplishment of the invention.

DETAILED DESCRIPTION OF THE PREFERRED EMBODIMENTS

Figure 1:
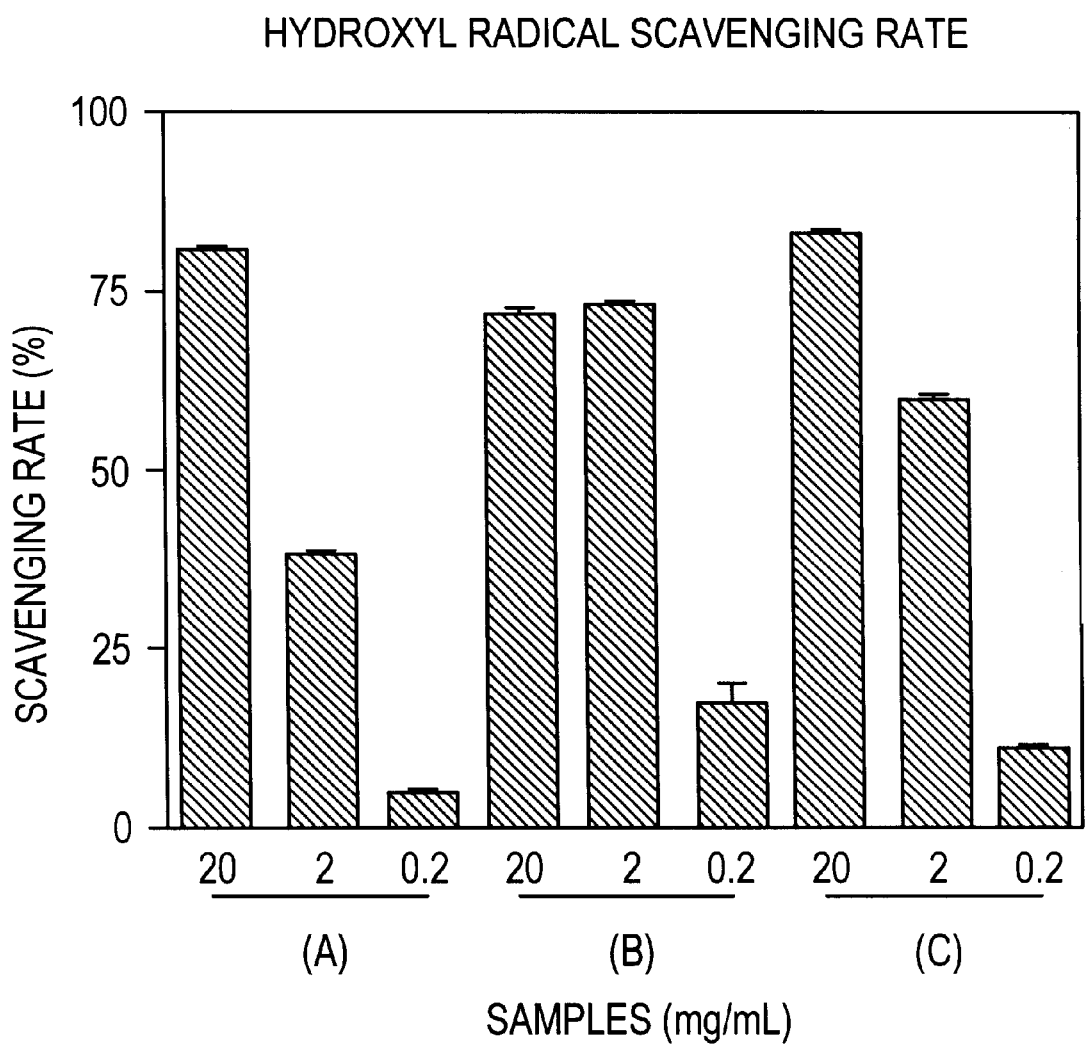
FIG. 1 illustrates hydroxyl radical scavenging activity.

"Maitake" (*Grifola frondosa*) is a mushroom which has traditionally been ingested as a food in Japan, and has been proven to be safe to eat, and known to contain immunopotentiating substances. However, there has been no report concerning active oxygen scavenging activity and cancer chemopreventing activity of a dry powder and a water or hot water extract of Maitake on the basis of scientific experiments.

Accordingly, the present invention provides the followings:

(1) An active oxygen scavenging agent comprising a dried Grifola, a dry Grifola powder and/or a Grifola extract;

(2) The active oxygen scavenging agent of item (1), wherein the dried Grifola is produced by drying a fresh Grifola at a temperature ranging from 50 to 90° C.;

(3) The active oxygen scavenging agent of item (1), wherein the dry Grifola powder is produced by: drying a fresh Grifola at a temperature ranging from 50 to 90° C. to give a dried Grifola; and then grinding the dried Grifola into powder using a milling apparatus;

(4) The active oxygen scavenging agent of item (1), wherein the Grifola extract is produced by extracting a fresh Grifola, a dried Grifola and/or a dry Grifola powder with water or hot water;

(5) The active oxygen scavenging agent of item (1), wherein the Grifola extract is produced by: extracting a fresh Grifola, a dried Grifola and/or a dry Grifola powder with water or hot water to give an extract; adding an alcohol to the extract; leaving the resultant solution to stand; and then removing matters floating on and/or in the solution and/or adhered to the wall surface of the vessel in which the solution is contained, from the solution;

(6) The active oxygen scavenging agent of item (1), wherein the Grifola extract is produced by: extracting a fresh Grifola, a dried Grifola and/or a dry Grifola powder with water or hot water to give an extract; adding an alcohol to the extract; leaving the resultant solution to stand; removing matters floating on and/or in the solution and/or adhered to the wall surface of the vessel in which the solution is contained, from the solution; removing the alcohol from the solution; and then drying the resultant solution;

(7) The active oxygen scavenging agent of any one of items (1) to (6), wherein the active oxygen to be scavenged with the scavenging agent is a hydroxyl radical and/or a superoxide anion radical;

(8) A food or animal feed with active oxygen scavenging activity, comprising the active oxygen scavenging agent of any one of items (1) to (7);

(9) A cancer chemopreventing agent comprising a dried Grifola, a dry Grifola powder and/or a Grifola extract;

(10) The cancer chemopreventing agent of item (9), wherein the target cancer to be treated by the cancer chemopreventing agent is gastrointestinal cancer;

(11) The cancer chemopreventing agent of item (9), wherein the target cancer to be treated by the cancer chemopreventing agent is colorectal cancer;

(12) The cancer chemopreventing agent of item (9), wherein the dried Grifola is produced by drying a fresh Grifola at a temperature ranging from 50 to 90° C.;

(13) The cancer chemopreventing agent of item (9), wherein the dry Grifola powder is produced by: drying a fresh Grifola at a temperature ranging from 50 to 90° C. to give a dried Grifola; and then grinding the dried Grifola into powder using a milling apparatus;

(14) The cancer chemopreventing agent of any one of items (9) to (11), wherein the Grifola extract is produced by extracting a fresh Grifola, a dried Grifola and/or a dry Grifola powder with water or hot water;

(15) The cancer chemopreventing agent of any one of items (9) to (11), wherein the Grifola extract is produced by: extracting a fresh Grifola, a dried Grifola and/or a dry Grifola powder with water or hot water to give an extract; adding an alcohol to the extract; leaving the resultant solution to stand; removing matters floating on and/or in the solution and/or adhered to the wall surface of the vessel in which the solution is contained, from the solution; removing the alcohol from the solution; and then drying the resultant solution;

(16) A process for producing a cancer chemopreventing agent, comprising: mixing a water-soluble excipient with a Grifola extract produced by extracting a fresh Grifola, a dried Grifola and/or a dry Grifola powder with water or hot water; and then spray-drying the resultant mixture;

(17) A process for producing a cancer chemopreventing agent comprising: mixing a water-soluble excipient with a Grifola extract produced by extracting a fresh Grifola, a dried Grifola and/or a dry Grifola powder with water or hot water to give an extract, adding an alcohol to the extract, leaving the resultant solution to stand, and then removing matters floating on and/or in the solution and/or adhered to the wall surface of the vessel in which the solution is contained from the solution; and then spray-drying the resultant mixture; and

(18) A food or animal feed for the chemoprevention of cancer, comprising the cancer chemopreventing agent of any one of items (9) to (17).

The term "an active oxygen scavenging agent (or scavenger)" or "a food or animal feed with an active oxygen scavenging activity" as used herein refers to any agent, medicine, in-between product of a medicine and a food (e.g., neutraceutical), nutritionally supplemental food, health food, general food and animal feed that can scavenge active oxygen species excessive for a living body of a human or other animal.

The term "a cancer chemopreventing agent (or cancer chemopreventer)" or "a food or animal feed for the chemoprevention of cancer" as used herein refers to any agent, medicine, in-between product of a medicine and a food (e.g., neutraceutical), nutritionally supplemental food, health food, general food and animal feed that can prevent or inhibit the development of cancer in a human and an animal.

In the present invention, the "Grifola" refers to "Maitake" (*Grifola frondosa*) or any of other related mushrooms including, for example, "Shiromaitake" (*Grifola albicans*), "Choreimaitake" (*Grifola umbellata*) and "Tonbimaitake" (*Grifola gigantea*), of which either or both of a fruit body and a micelium may be used. Recently, the artificial cultivation of a fruit body of Maitake has been succeeded. Therefore, it is preferable to use a fruit body of Maitake from the viewpoint of stable resource supply.

A dried Grifola used in the present invention may be prepared by drying a fresh Grifola by any drying method selected among sun drying, drying in a warming or heating chamber, hot air drying, freeze drying and an appropriate combination thereof. For example, the drying process is preferably performed by gradually raising the temperature from 50° C. to 90° C. especially from 60° C. to 80° C.

A dried Grifola is then ground into powder with a milling apparatus to prepare a dry Grifola powder. When a dried Grifola is used as it is, it may be ground into coarse or fine powder and may be of any particle size depending on the intended use. For example, in the application for a human body, it may be ground into powder or fine powder having a particle size of 100 mesh or smaller; whereas for the use in an animal feed, it may be ground into coarse powder having a particle size of 100 mesh or larger, which may be mixed into an animal feed product.

For the preparation of a Grifola extract, the extraction treatment may be performed at room temperature or under heating for a period of time from 5 minutes to 3 hours. For the short-time extraction, the extraction treatment may be performed at 100° C. or higher under pressure, for example, at about 120° C. for from about 5 minutes to about 1 hours under pressure using an autoclave. Water used for the extraction may be any type, such as distilled water, purified water, ion exchanged water, tap water or natural water. The amount of water used for the extraction is, for example, from 4 volumes to appropriate volumes, preferably from 10 volumes to 20 volumes, based on 1 weight of a dried Grifola or a dry Grifola powder. When a fresh Grifola is used, water is used in an amount from 2 volumes to appropriate volumes, preferably from about 5 volumes to about 10 volumes, based on 1 weight of the fresh body. After the extraction, the resultant solution is filtered (e.g., with a filter paper or cloth) or centrifuged, thereby yielding the intended water extract.

The water extract may be subjected to an additional treatment, such as purification by the addition of an alcohol, if necessary. For example, an alcohol may be added to the water extract in a final concentration of 20–70% by volume, preferably 30–60% by volume. Examples of the alcohol include methanol and ethanol. After the addition of the alcohol, the resultant solution is left to stand for 1 hour or longer, whereby matters floating on or in the solution or adhered to the wall surface of the vessel in which the solution is contained, appear. The matters are then removed from the solution by filtration, aspiration (e.g., pipetting), straining out with a meshed material, or the like.

The purified extract may be used as it is or the alcohol may be removed therefrom before use. The purified extract may also be condensed into a fluid extract, or dried by any conventional drying method (e.g., condensation drying, spray drying, vacuum drying, or freeze drying) to give a dry extract powder.

It has been known that the extract contains a polysaccharide (e.g., β-glucan) or a complex of a polysaccharide and a protein. Therefore, to purify and isolate such a component, the extract may be additionally subjected to a conventional purification procedure, such as precipitation, chromatography and gel filtration.

The active oxygen scavenging agent or cancer chemopreventing agent of the present invention may be used as it is. Alternatively, it may be mixed with a suitable excipient to be formulated into a powder, tablet, granule or solution, or mixed with a food or animal feed preparation.

When applied to a medicine, food or animal feed, the Grifola extract powder is preferably used in the form of a preparation in which it is dispersed in a suitable excipient, due to its high hygroscopicity. In this case, the extract powder may be simply mixed with a suitable excipient. However, it is preferable to formulate in the following manner.

A Grifola extract or a purified fraction thereof is mixed with a water- or hot water-soluble excipient (e.g., dextrin, cyclodextrin or lactose) to yield a mixture, if necessary, water or hot water is added to the mixture, and the liquid mixture is then spray dried.

The mixing ratio between the extract or purified fraction thereof and the excipient may vary depending on the intended use. However, the mixing ratio of 1:1 (on the weight basis) is preferable, because a formulation with this mixing ratio can considerably improve the undesirable hygroscopicity of the dried extract and is therefore suitable for a wide range of applications.

When cyclodextrin is used as the excipient, it may be of any type, including α-form, β-form and γ-form, but is preferably of α-form or γ-form because of its higher water solubility. In the case where water or hot water is added to the mixture of the extract and the excipient to yield a liquid preparation, it is preferable that water or hot water is added so that the Brix value of the resultant liquid preparation becomes 50% or lower, preferably from 30 to 40%. The liquid preparation is then spray dried with a spray drying apparatus, thereby producing the intended formulation.

EXAMPLE 1

Dry Maitake Powder (A)

Fresh Maitake (*Grifola frondosa*) fruit bodies were harvested. The stems and caps were placed on the trays in a tray drying chamber, and then allowed to dry for approximately one day by feeding hot air of about 60–80° C. to the trays. In this drying process, the temperature of the hot air was gradually elevated starting from 60° C. to finally 80° C. The dried stems and caps were ground to powder with a mill, thereby giving a dry Maitake powder.

EXAMPLE 2

Maitake Extract (B)

Fresh Maitake fruit bodies (2.5 kg) were sliced into pieces of 2–3 cm thick, and then soaked in a 10-L water bath (95–100° C.) to be extracted. The resultant extract solution was filtered, thereby giving a dark brown extract with a Brix value of 1%. The extract was condensed at 75–80° C. under reduced pressure using a vacuum evaporator to give a condensed solution with a Brix value of 5%. The condensed solution was spray dried with a spray drying apparatus, thereby giving a grayish brown, dry Maitake hot water extract powder (60 g).

EXAMPLE 3

Purified Maitake Extract (C)

A dry powder (100 g) of fruit bodies of Maitake was treated in ion exchange water (1000 mL) at 120° C. for 30 minutes under pressure at 2 atoms. The resultant solution was filtered to give a dark brown extract solution (600 mL). The extract solution was condensed under reduced pressure to a volume of 200 mL, and then added with 95% ethanol (210 mL). The resultant mixed solution was left to stand for about 18 hours, whereby brown materials floating on and in the solution and adhered on the wall surface of the vessel in which the solution was contained, appeared. The materials were strained out from the solution with a wire cloth to give a brown solution. The solution was treated under reduced pressure to remove the alcohol therefrom. The resultant solution was further condensed under reduced pressure (24–42 kPa) at 70–80° C. until the Brix value of the solution reached 30%, thereby giving a dark brown condensed solution.

The condensed solution was spray dried with a spray drying apparatus, whereby a brown fine powder (19 g) with sweet smell characteristic of Maitake was obtained. The analysis of this product revealed that it consisted mainly of carbohydrate including polysaccharaides (e.g., β-glucan) and proteins and was soluble in water, and its aqueous solution was neutral or weakly acidic.

EXAMPLE 4
Purified Maitake Extract

A dry Maitake powder (2 kg) was treated in water (30 L) under pressure at 120° C. for 30 minutes. The resultant solution was filtered to give a dark brown extract solution (20 L). The extract solution was condensed under reduced pressure to a volume of 6 L, and then added with 95% alcohol (6.5 L). The resultant mixed solution was left to stand at a temperature of 10° C. or lower for from several hours to a half day, whereby brown materials floating on and in the solution and adhered on the wall surface of the vessel in which the solution was contained, appeared. The materials were strained out from the solution with a wire cloth to give a brown solution. The solution was treated under reduced pressure to remove the alcohol therefrom. The resultant solution was condensed under reduced pressure until the Brix value of the solution reached 30%, thereby giving a dark brown condensed solution.

The condensed solution was spray dried with a spray drying apparatus, whereby a brown powder (395 g) with sweet smell characteristic of Maitake was obtained.

EXAMPLE 5
Maitake Extract-containing Powder

Since the Maitake extract powder prepared as described in Example 4 was hygroscopic, it was mixed with dextrin ("PINE-DEX #100; Matsutani Kagaku Kogyo Co., Ltd.). at a mixing ratio of 1:1 (on the weight basis). The mixture was dissolved in hot water so that the resultant solution has a Brix value of 30–40%. The solution was spray dried with a spray drying apparatus, thereby giving a powdery product containing a Maitake extract.

EXAMPLE 6
Determination of Hydroxyl Radical Scavanging Activity

Aqueous solutions of the Maitake-derived products (A), (B) and (C) obtained in Examples 1–3, respectively, were prepared at concentrations of 0.2 mg/mL, 2.0 mg/mL and 20.0 mg/mL, and then determined for hydroxyl radical scavenging activity by the Fenton reaction method as follows.

Each of the aqueous solutions (50 μL, each) was added with a 1 mM $FeSO_4$-DTAPAC (diethylenetriamine pentaacetic acid) solution (75 μL), and then a 10-fold dilution (20 μL) of DMPO (5,5-dimethyl-1-pyrroline-N-oxide) and 0.1 mM $H_2O_2$ (75 μL) were further added thereto. After stirring for 2 seconds, the resultant solution was taken in a flat cell, and determined for the amount of generated hydroxyl radicals in terms of DMPO-OH using an electron spin resonance (ESR) spectrometer (JES-FR30) [Japan Electron Optics Laboratory Co., Ltd. (JEOL)]. The sweeping was started 60 seconds after the addition of $H_2O_2$.

The conditions for the spectral analysis by ESR spectrometer were as follows:

magnetic field sweep width: 335.6 mT;

magnetic field modulation: 0.1 mT;

amplification rate: 125;

sweep time: 2 min.;

response time: 0.1 sec.; and temperature of measurement: room temperature.

The results are shown in FIG. 1. As a result, it was found that the products (A) and (C) exerted 70% or higher hydroxyl radical scavenging activity at 20 mg/mL and the product (B) exerted even at 2 mg/mL, and the highest activity was observed for the product (C) at 20 mg/mL.

EXAMPLE 7
Superoxide Anion Radical Scavenging Activity
Superoxide Dismutase (SOD)-like Activity Using the same aqueous solutions of the Maitake-derived products (A), (B) and (C) as used in Example 6, the superoxide dismutase (SOD)-like activity of each solution was determined by the spin trap method using ERS spectrometer (JES-FR30; JEOL) as follows.

A hypoxanthine (HPX) solution (2 mM), a DETAPAC solution (5.5 mM), a series of SOD solutions (0.1–50 U/mL) and a xanthine oxidase (XOD) solution (0.4 U/mL) were separately prepared using 0.2 mM phosphate buffer solution as a solvent. A trapping agent DMPO (15 μL, 9.2 M) was added to each of the HPX solution (50 μL), the DETAPAC solution (35 μL) and each of the SOD solutions (50 μL), and the resultant mixed solution was further mixed with the XOD solution (50 μL). The resultant solution was measured for the spectrum of generated $O_2^-$-adducts in a quartz cell.

The signal intensity of the $O_2^-$-adducts was calculated as a relative value to the signal intensity of the internal standard Mn, and a calibration curve was prepared using the determined values at different concentrations of SOD. In the same manner, each of the aqueous solutions (50 μL, each) of the Maitake-derived products (A), (B) and (C) was also measured for the spectrum of generated $O_2^-$-adducts in a quartz cell. The inhibition rate (%) relative to a control (distilled water) was determined, and the scavenging rate (%) was calculated as a SOD concentration (corresponding to the SOD activity of the test solution) from the calibration curve.

Figure 2:
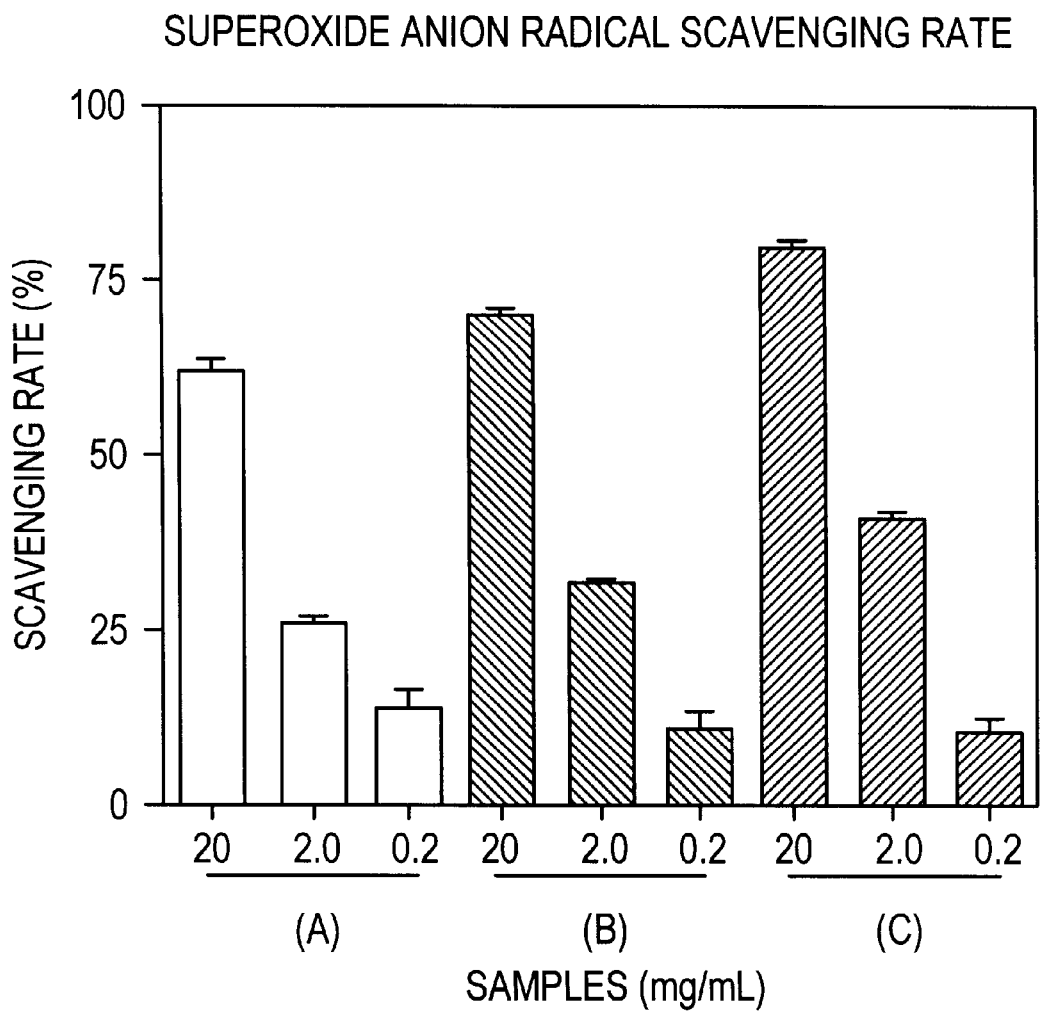
FIG. 2 illustrates superoxide anion radical scavenging activity.
Figure 3:
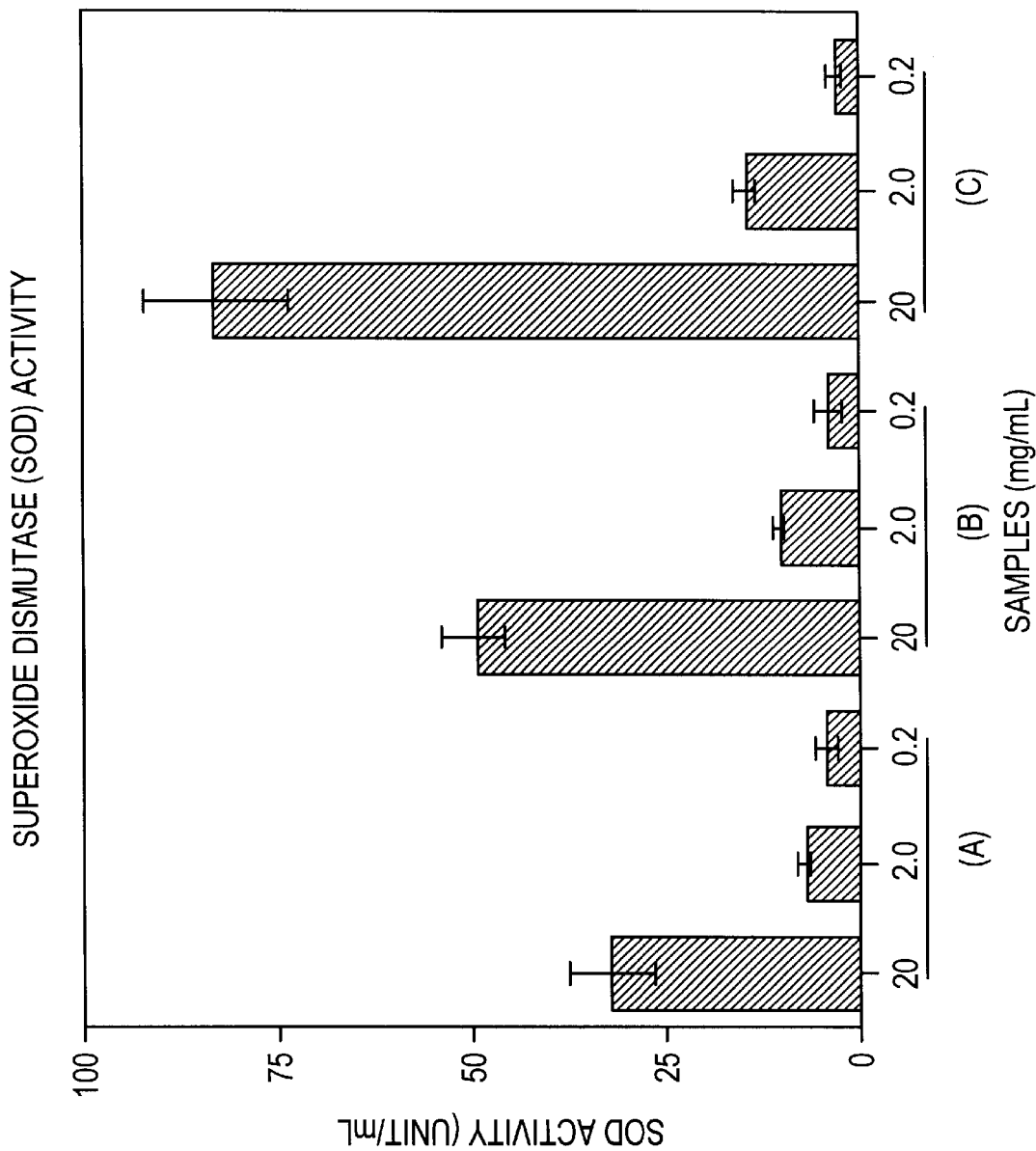
FIG. 3 illustrates superoxide dismutase (SOD)-like activity.

The results are shown in FIGS. 2 and 3. As a result, it was found that all of the products (A), (B) and (C) showed high superoxide anion radical scavenging activity and SOD-like activity at 20 mg/mL, and both the activities were highest in the product (C).

The results of Examples 6 and 7 clearly demonstrate that all of the dry Maitake powder, Maitake extract and purified Maitake extract according to the present invention have hydroxyl radical scavenging activity, superoxide anion radical scavenging activity and SOD-like activity.

EXAMPLE 8
Cancer Chemoprevention Test
(1) Test Method

In this test, male Donryu rats (4-week old, 12–13 rats per group) were used as the test animals. In the test groups, a feed blend containing 5% of the Maitake extract-containing powder prepared as in Example 4 through Example 5 (corresponding to 2.5% of the Maitake extract) in a base feed was fed to 12 rats (hereinafter, referred to as "A-5" group); and a feed blend containing 20% of the dry Maitake powder prepared as in Example 1 in the base feed was fed to 12 rats (hereinafter, referred to as "A-20" group). In the control group, only the base feed was fed to 13 rats (hereinafter, referred to as "A-C" group). These three groups were examined for cancer chemopreventing effect in the following manner.

Azoxymethane (AOM) was dissolved in physiological saline, and the resultant solution was administered subcutaneously into the back of the rats at a dose of 7.5 mg/kg per rat at intervals of a week for 10 times, and thirty weeks after the final administration, all of the rats were sacrificed. Until the rats were sacrificed, the rats were individually observed the physical conditions and measured for the body weight once a week. After the rats were sacrificed, the large intestine was dissected, and then the number, the location and the size (longer diameter×shorter diameter) of the tumors developed in the colon were determined. In addition, tissues from one or more regions in the colon where the tumors were developed were dissected, fixed in a 10% formalin solution, embedded in paraffin, and then stained by any one of hematoxylin-and-eosin (H.E.) and periodic acid-Schiff stain (PAS) methods for histologic examination.

The base feed used in this experiment was a commercially available feed specified for mice, rats and hamsters, "MF" (Oriental Yeast Co., Ltd.) having the following composition.

| General composition (in 100 g): | |
| --- | --- |
| Water | 7.8 g |
| Crude proteins | 23.8 |
| Crude lipids | 5.1 |
| Crude ash | 6.1 |
| Crude fibers | 3.2 |
| Soluble non-nitrogenous matters | 54.0 |
| Total | 100.0 |
| | (calorie: 357 kcal/100 g) |

(2) Test Results
(i) Comparison of the Number of Tumors

TABLE 1

| | Number of tumors/rat | | |
| --- | --- | --- | --- |
| | A-C | A-5 | A-20 |
| Average | 3.4 | 1.9 | 0.3 |
| Standard deviation | 2.4 | 1.2 | 0.5 |
| Standard error | 0.67 | 0.34 | 0.13 |

Figure 4:
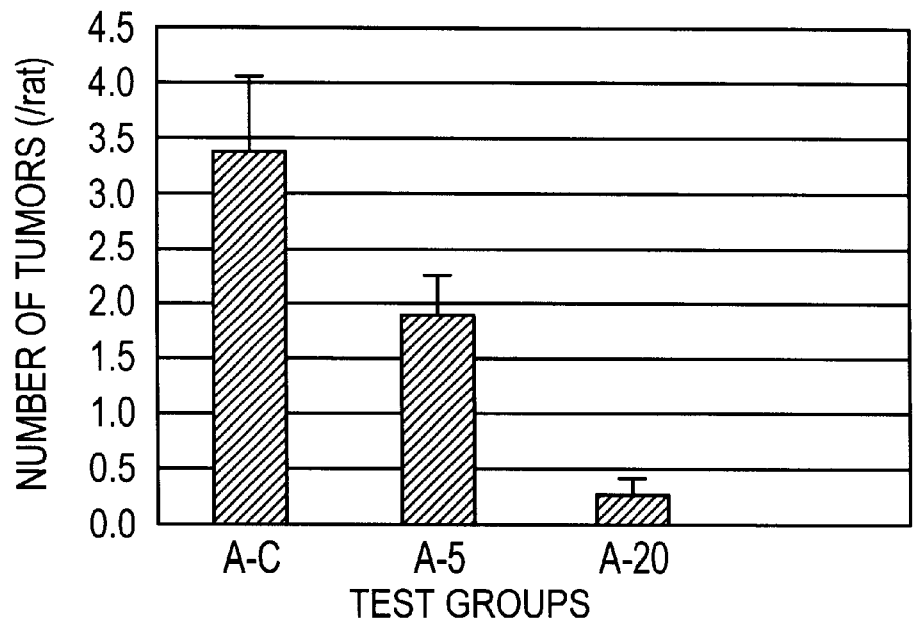
FIG. 4 illustrates the comparison of the number of tumors in cancer chemopreventing test.

As shown in Table 1 and FIG. 4, in the control group [A-C], the average number of tumors per rat was 3.4; whereas in the test group [A-5] [i.e., a group fed a feed blend containing 5% of the Maitake extract powder (corresponding to 2.5% Maitake extract)], the average number of tumors per rat was 1.9 (55.9% relative to the number in the control group), and in the test group [A-20] (i.e., a group fed a feed blend containing 20% of dry Maitake powder), the average number of tumors per rat was 0.3 (8.8% relative to the number in the control group). These results clearly demonstrate that the administration of the Maitake extract and the dry Maitake powder of the present invention can effectively chemoprevent and inhibit the tumor development.

The t-test revealed that there was a significant difference between the result for [A-20] and the result for [A-C] with a level of significance of less than 1%.

(ii) Comparison of the Tumor Size (by Area)

TABLE 2

| | Tumor size (mm$^2$)/rat | | |
| --- | --- | --- | --- |
| | A-C | A-5 | A-20 |
| Average | 78.1 | 61.9 | 31.7 |
| Standard deviation | 58.5910425 | 60.6022177 | 78.2575391 |
| Standard error | 16.3 | 17.5 | 22.6 |

Figure 5:
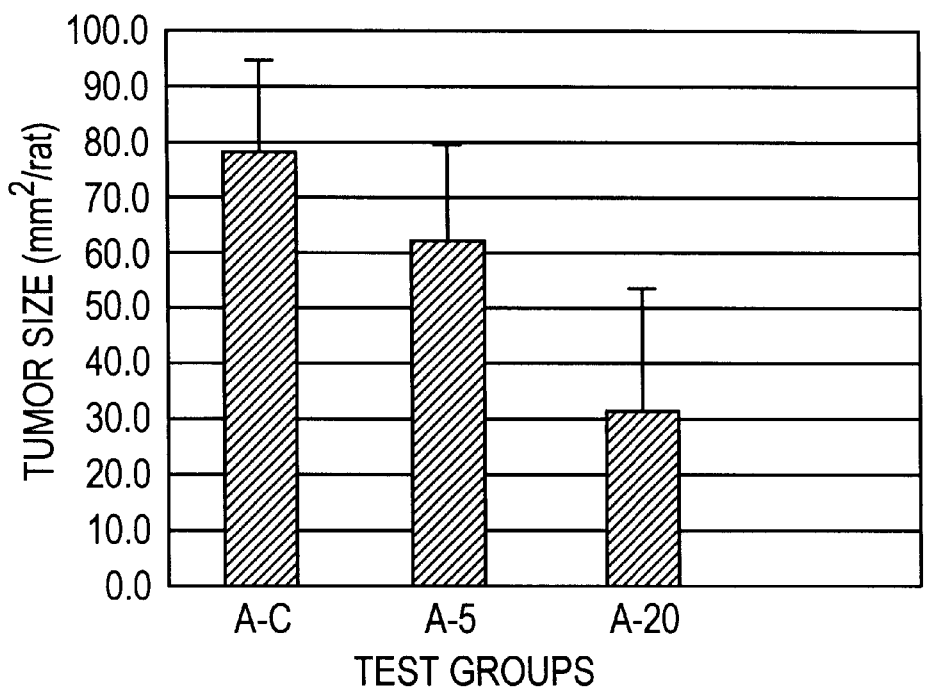
FIG. 5 illustrates the comparison of the tumor size (by area) in cancer chemopreventing test.

As shown in Table 2 and FIG. 5, in the control group [A-C], the average tumor size per rat was 78.1 mm$^2$; whereas in the test groups, the average tumor size per rat was 61.9 mm$^2$ in [A-5] [i.e., a group fed a feed blend containing 5% of the Maitake extract powder (corresponding to 2.5% Maitake extract)], and 31.7 mm$^2$ in [A-20] (i.e., a group fed a feed blend containing 20% of dry Maitake powder).

These results clearly demonstrate that the Maitake-derived products of the present invention can effectively reduce the tumor size.

(iii) Change in Body Weight

For the verificational purpose, the change in the average body weight per rat was determined. However, no significant difference was observed between the test groups and the control group.

In the above Examples, tests were performed on the colorectal cancer development. However, the Maitake extract-containing powder and dry Maitake powder of the present invention will also have effective chemopreventing activity against other intestinal cancer including gastrointestinal cancer, as well as other kinds of cancer.

What is claimed is:

1. A process for producing an active oxygen scavenging agent comprising a dried body of Grifola, wherein the process comprises producing the dried body of Grifola by gradually raising the temperature of the body of Grifola from 50° C. to 90° C. for a sufficient time .

2. The process for producing an active oxygen scavenging agent of claim 1 wherein the step of producing comprises gradually raising the temperature of the body of Grifola from 60° C. to 80° C.

3. A process for producing an active oxygen scavenging agent comprising a dried Grifola powder, wherein the process comprises drying a fresh body of Grifola by gradually raising the temperature of the fresh body of Grifola from 50° C. to 90° C. for a sufficient time to produce a dried Grifola and then grinding the dried Grifola into a powder using a milling apparatus.

4. The process for producing an active oxygen scavenging agent of claim 3, wherein the step of drying a fresh body of Grifola comprises gradually raising the temperature of the fresh body of the Grifola from 60° C. to 80° C.

* * * * *